(12) United States Patent
Shlomoff

(10) Patent No.: US 12,721,662 B2
(45) Date of Patent: Sep. 1, 2026

(54) SYSTEMS AND METHODS FOR TREATING PERIPROSTHETIC FRACTURES

(71) Applicants: KANFIT 3D., Nof Hagalil (IL); Liraz Shlomoff, Rehovot (IL)

(72) Inventor: Liraz Shlomoff, Rehovot (IL)

(73) Assignees: Liraz Shlomoff, Rehovot (IL); KANFIT 3D., Nof Hagalil (IL)

( * ) Notice: Subject to any disclaimer, the term of this patent is extended or adjusted under 35 U.S.C. 154(b) by 395 days.

(21) Appl. No.: 17/414,032

(22) PCT Filed: Dec. 16, 2019

(86) PCT No.: PCT/IL2019/051372

§ 371 (c)(1),
(2) Date: Jun. 15, 2021

(87) PCT Pub. No.: WO2020/129053

PCT Pub. Date: Jun. 25, 2020

(65) Prior Publication Data

US 2022/0022926 A1 Jan. 27, 2022

Related U.S. Application Data

(60) Provisional application No. 62/781,172, filed on Dec. 18, 2018.

(51) Int. Cl.
*A61B 17/72* (2006.01)
*A61B 17/16* (2006.01)
(Continued)

(52) U.S. Cl.
CPC ........ *A61B 17/7241* (2013.01); *A61B 17/164* (2013.01); *A61B 17/683* (2013.01); *A61F 2/3676* (2013.01); *A61F 2002/368* (2013.01)

(58) Field of Classification Search
CPC ............ A61B 17/7241; A61B 17/7258; A61B 17/7266; A61B 17/744; A61B 17/72;
(Continued)

(56) References Cited

U.S. PATENT DOCUMENTS 5,002,578 A * 3/1991 Luman ...................... A61F 2/36 623/22.46
5,167,619 A * 12/1992 Wuchinich ....... A61B 17/32002 606/171

(Continued)

FOREIGN PATENT DOCUMENTS

CN 107468324 12/2017
EP 1344505 A2 9/2003

(Continued)

OTHER PUBLICATIONS

PCT International Search Report for International Application No. PCT/IL2019/051372, mailed Apr. 14, 2020, 2pp.

(Continued)

*Primary Examiner* — Julianna N Harvey
(74) *Attorney, Agent, or Firm* — The Roy Gross Law Firm, LLC; Roy D. Gross

(57) ABSTRACT

The present invention relates, in some embodiments thereof, to orthopedic implantable devices for treatment of periprosthetic bone fractures, the devices include an elongated cylindrical shaft extending between a distal end and a proximal end, wherein a proximal portion extends from the proximal end, the proximal portion sized and shaped to allow for an engagement with a distal tip of a preexisting bone implant, the proximal portion comprising at least one longitudinal slot extending from the proximal end and providing a relatively flexible proximal portion configured to mate with various sizes and shapes of preexisting bone implants.

4 Claims, 6 Drawing Sheets

(51) Int. Cl.
*A61B 17/68* (2006.01)
*A61F 2/36* (2006.01)

(58) Field of Classification Search
CPC ............ A61B 17/32002; A61B 17/164; A61B 17/8847; A61B 2017/32007; A61B 17/7283; A61B 17/7275; A61F 2002/3674; A61F 2/3676; A61F 2002/3694
See application file for complete search history.

(56) References Cited

U.S. PATENT DOCUMENTS

| | | | | |
|---|---|---|---|---|
| 5,620,445 | A * | 4/1997 | Brosnahan | A61B 17/72 606/68 |
| 8,668,692 | B1 * | 3/2014 | Lindvall | A61B 17/72 606/62 |
| 10,561,411 | B1 * | 2/2020 | Cole | A61B 17/8869 |
| 2011/0270256 | A1 * | 11/2011 | Nelson | A61B 17/1659 606/85 |
| 2012/0041395 | A1 | 2/2012 | Sweeney | |
| 2013/0197551 | A1 * | 8/2013 | Yoon | A61B 17/22 606/170 |
| 2014/0074250 | A1 * | 3/2014 | Podolsky | A61F 2/34 623/22.42 |
| 2015/0282935 | A1 * | 10/2015 | Kuldjanov | A61F 2/3859 623/23.18 |
| 2017/0071588 | A1 * | 3/2017 | Choi | A61B 17/0218 |
| 2018/0200065 | A1 * | 7/2018 | Segina | A61F 2/3859 |

FOREIGN PATENT DOCUMENTS

| | | | |
|---|---|---|---|
| EP | 1402856 | A1 | 3/2004 |
| WO | 91/11155 | A1 | 8/1991 |

OTHER PUBLICATIONS

PCT Written Opinion for International Application No. PCT/IL2019/051372, mailed Apr. 14, 2020, 11pp.

PCT International Preliminary Report on Patentability for International Application No. PCT/IL2019/051372, issued Jun. 16, 2021, 12pp.

* cited by examiner

SYSTEMS AND METHODS FOR TREATING PERIPROSTHETIC FRACTURES

CROSS REFERENCE TO RELATED APPLICATIONS

This application is a National Phase of PCT Patent Application No. PCT/IL2019/051372having International filing date of Dec. 16, 2019, which claims the benefit of priority of U.S. Provisional Patent Application No. 62/781,172, filed Dec. 18, 2018, the contents of which are all incorporated herein by reference in their entirety.

FIELD OF THE INVENTION

The present invention relates, in some embodiments thereof, to orthopedic implantable devices for treatment of periprosthetic bone fractures, the devices include an elongated cylindrical shaft extending between a distal end and a proximal end, wherein a proximal portion extends from the proximal end, the proximal portion sized and shaped to allow for an engagement with a distal tip of a preexisting bone implant, the proximal portion comprising at least one longitudinal slot extending from the proximal end and providing a relatively flexible proximal portion configured to mate with various sizes and shapes of preexisting bone implants.

BACKGROUND OF THE INVENTION

Periprosthetic fractures (PF) are fractures caused or associated with an orthopedic implant, such as a replacement or internal fixation device. The overall incidence of PF is increasing continuously due to the growing number of primary joint arthroplasties and revision surgeries.

PF are mainly associated with fractures about the hip, and knee. Current procedures for the treatment of PF typically involve plating with or without cerclage wires in case of stable stems, replacement of the preexisting implant by a longer version implant for loose stems, plating with or without cerclage wires and/or bone grafting, or even total femoral replacement in cases of loose stems and poor bone stock.

U.S. Pat. No. 8,668,692 relates to an intramedullary linkage device for treatment of peri-prosthetic long bone fractures, system for long bone fracture treatment in the setting of pre-existing intramedullary implant using an intramedullary linkage device and intramedullary fracture fixation device, and methods of treating peri-prosthetic long bone fracture in the setting of pre-existing intramedullary implant using an intramedullary linkage device and intramedullary fracture fixation device.

Nevertheless, those surgical procedures are cumbersome and suboptimal, and accompanied with high complications rate. There is thus a need for improved treatments of PF.

SUMMARY OF THE INVENTION

Objects of the invention are achieved by providing systems, devices and methods for effectively treating a periprosthetic fracture in a subject in need thereof.

Objects of the invention are achieved by providing systems, devices and methods which afford an orthopedic implantable device configured to engage in mating match, or in a friction fit with various sizes and/or shapes of preexisting prostheses.

According to a first aspect, the present invention provides an orthopedic implantable device for treatment of periprosthetic bone fractures, the device comprising an elongated cylindrical shaft extending between a distal end and a proximal end, wherein a proximal portion extends from the proximal end, the proximal portion sized and shaped to allow an engagement with a distal tip of a preexisting bone implant, the proximal portion comprising at least one longitudinal slot extending from the proximal end and allowing the engagement with the preexisting bone implant in a radial expandable manner.

According to another aspect, the present invention provides an orthopedic implantable device for treatment of periprosthetic bone fractures, the device comprising an elongated cylindrical shaft extending between a distal end and a proximal end, wherein a proximal portion extends from the proximal end, the proximal portion sized and shaped to allow an engagement with a distal tip of a preexisting bone implant, and wherein the shaft being oblique in a vertical axis of the proximal end.

In one or more embodiments, the proximal portion having a conical shape wherein the outer and/or inner diameter decreases from proximal to distal. In one or more embodiments, the proximal portion having a conical canal or cavity.

In one or more embodiments, the proximal portion is configured to disconnect or disengage the shaft.

In one or more embodiments, at least the proximal portion being hollowed.

In one or more embodiments, the device further comprising a distal potion and wherein at least the proximal portion and the distal portion being hollowed.

In one or more embodiments, the device is hollowed from proximal to distal.

In one or more embodiments, the proximal end being oblique in a vertical axis of the shaft.

In one or more embodiments, an angle of less than about 90° extends between a longitudinal axis and a vertical axis of the shaft at the proximal end.

In one or more embodiments, the slot has a substantially U-like, or V-like shape.

In one or more embodiments, the proximal portion is expandable allowing adaptation to various sizes and/or shapes of the distal tip of a preexisting bone implant.

In one or more embodiments, the proximal portion has a rounded, or an elliptical cross section.

In one or more embodiments, the device further comprising a distal portion extending from the distal end, the distal portion being internally threaded allowing manipulation of the shaft within a bone by a tool comprising a body with complementary external threaded proximal end.

In one or more embodiments, the device further comprising at the distal portion one or more cross channels for receiving bone screw(s), thereby stabilizing the shaft within a bone.

In one or more embodiments, the bone screw(s), is uniplanar or multiplanar.

In one or more embodiments, the device is configured to be inserted within the medullary cavity.

In one or more embodiments, the shaft has a length within the range of about 50 mm to about 350 mm.

In one or more embodiments, the slot has a length within the range from about 30 mm to about 170 mm.

In one or more embodiments, the slot has a length within the range from about 30 mm to about 100 mm.

In one or more embodiments, the slot has a maximal width within the range of about 5 mm to about 20 mm.

In yet a further aspect the present invention provides a spatula for the removal of a material from bone cavity, the spatula comprising a handle and a bowl coupled to the handle, the bowl defining a cavity, the spatula sized and shaped to allow insertion thereof within a bone cavity. In one or more embodiments, the handle comprises a slight curvature to conform to a bow within the bone. In one or more embodiments, the curvature is a forward or a backward curvature.

In one or more embodiments, the entire spatula is substantially aligned along a longitudinal plane such that the bow portion continuously extends from the handle and longitudinally aligned there with. In one or more embodiments, the bow portion and the handle are substantially aligned along a longitudinal plane with respect to each other.

In one or more embodiments, the spatula having a length of between about 150 mm and up to about 500 mm. In one or more embodiments, the spatula having a width of between about 5 mm and up to about 15 mm. In one or more embodiments, the length of the bowl portion is between about 10 mm and up to about 100 mm. In one or more embodiments, the curvature has a radius of between about 5 mm and about 100 mm.

In yet a further aspect, the preset invention provides a method for the treatment of periprosthetic bone fracture, the method comprising:

- preparing a bone canal of a fractured bone with a preexisting bone implant;
- inserting an orthopedic implantable device as herein described into the bone canal;
- engaging the orthopedic implantable device with the preexisting bone implant; and
- stabilizing connection of the orthopedic implantable device to the bone.

In one or more embodiments, preparing a bone canal comprises removing/grinding/spitting a material from the bone canal, thereby providing space around the preexisting implant.

In one or more embodiments, the material is a bone tissue and/or bone cement.

In one or more embodiments, the tissue removal is conducted using a spatula as herein described.

In one or more embodiments, stabilizing connection of the orthopedic implantable device is performed using screws linking a distal portion of the orthopedic implantable device to the bone.

In one or more embodiments, the method further comprising inserting along with the orthopedic implantable device an insertion handle configured to allow the insertion of the orthopedic implantable device.

In one or more embodiments, the method further comprising inserting a device for locking the screws.

In one or more embodiments, the method further comprising expanding the orthopedic implantable device using a nail extender, the nail extender comprises a longitudinal shaft having a proximal end configured to engage with a distal end of the orthopedic implantable device. In one or more embodiments, the proximal end of the nail extender having a size and shape being essentially similar to the size and shape of the distal end of the orthopedic implantable device. In one or more embodiments, an outer diameter of the proximal end of the nail extender being essentially similar to the outer diameter of the distal end of the orthopedic implantable device.

In one or more embodiments, the nail extender includes a connection bolt allowing secure connection between the distal end of the orthopedic implantable device and the proximal end of the nail extender.

In yet a further aspect the present invention provides a kit for treatment of periprosthetic bone fractures, the kit comprising an orthopedic implantable device as herein described; and a spatula as herein described, the spatula configured for removing a material from the vicinity of a preexisting bone implant prior to an insertion of the orthopedic implantable device.

In one or more embodiments, the kit further comprising an insertion handle configured to allow the insertion of the orthopedic implantable device within a bone canal.

In one or more embodiments, the kit further comprising a nail extender configured to engage with a distal end of the orthopedic implantable device, the nail extender comprising a hollowed cylindrical shaft extending between a proximal end and a distal end, wherein the proximal end sized and shaped essentially similar to the size and shape of the distal end of the orthopedic implantable device.

In one or more embodiments, an outer diameter of the proximal end of the nail extender being essentially similar to the outer diameter of the distal end of the orthopedic implantable device.

In one or more embodiments, the nail extender includes a connection bolt allowing a secure connection between the distal end of the orthopedic implantable device and the proximal end of the nail extender.

In one or more embodiments, the distal end of the orthopedic implantable device is internally threaded and wherein the bolt configured to engage with the internal thread of the orthopedic implantable device.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 schematically illustrates top views of exemplary spatulas, according to some embodiments of the invention.

FIG. 2 schematically illustrates side views of the spatulas of FIG. 1, according to some embodiments of the invention.

Figures 3, 4A:
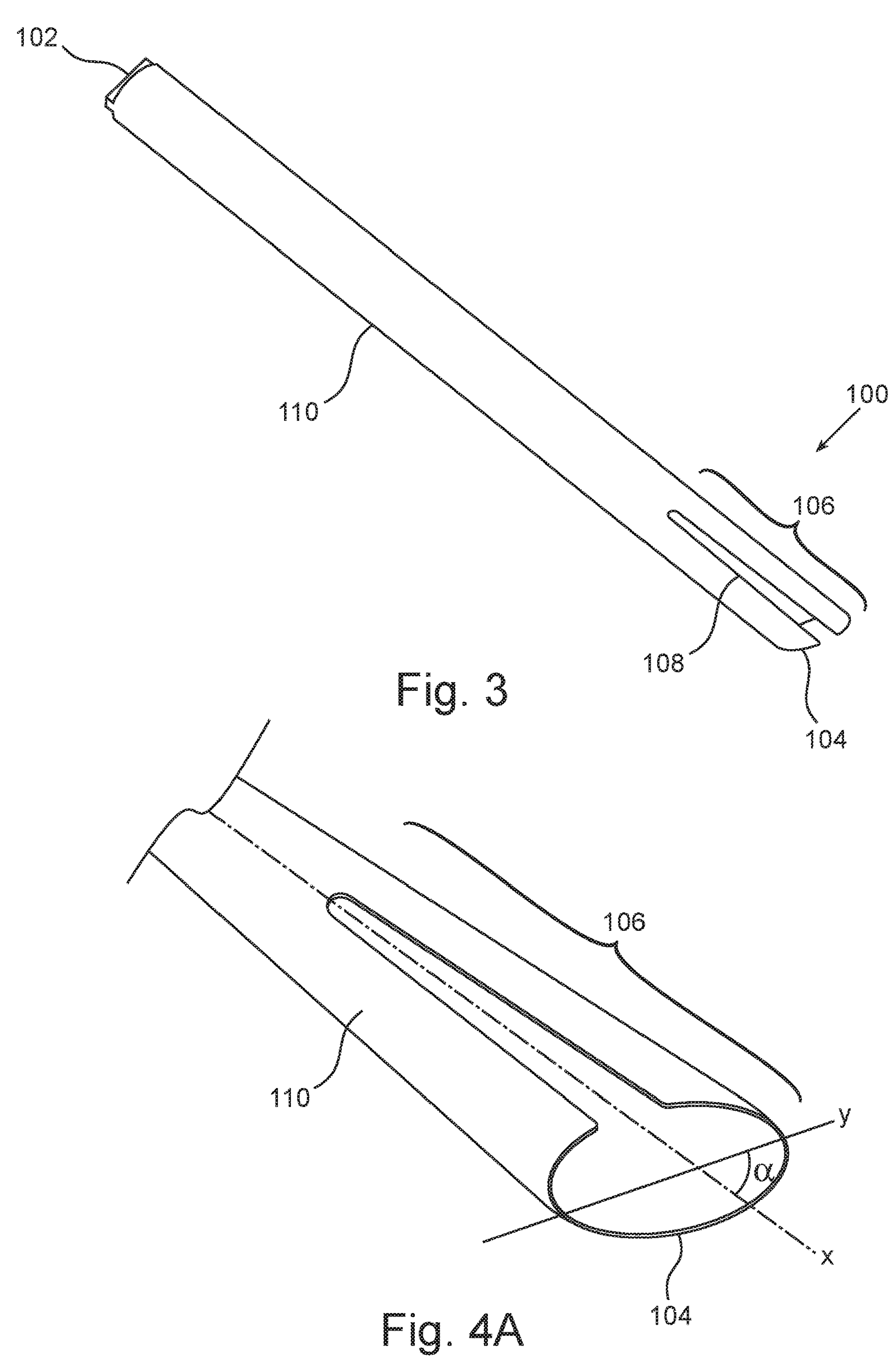
FIG. 3 is an isometric side view illustrating the herein disclosed orthopedic implantable device, according to some embodiments of the invention.
FIGS. 4A-4B are isometric side views illustrating proximal portions of the herein disclosed orthopedic implantable device, according to some embodiments of the invention.

It should be appreciated that for simplicity and clarity of illustration, elements shown in the figures have not necessarily been drawn to scale. For example, the dimensions of some of the elements are exaggerated relative to each other for clarity. Further, where considered appropriate, reference numerals have been repeated among the figures to indicate corresponding elements.

DETAILED DESCRIPTION OF THE INVENTION

It is understood that the invention is not limited to the particular methodology, devices, items or products etc., described herein, as these may vary as the skilled artisan will recognize. It is also to be understood that the terminology used herein is used for the purpose of describing particular embodiments only and is not intended to limit the scope of the invention. The following exemplary embodiments may be described in the context of exemplary orthopedic devices for ease of description and understanding However, the invention is not limited to the specifically described products and methods and may be adapted to various applications without departing from the overall scope of the invention. All ranges disclosed herein include the endpoints. The use of the term "or" shall be construed to mean "and/or" unless the specific context indicates otherwise.

Periprosthetic bone fracture is a phenomenon associated with bone implants during surgery or post-operatively. Periprosthetic bone fractures are commonly known as fractures occurring at the vicinity of joint replacement prostheses. The correct surgical management choice of those fractures is challenging and, in many cases, involves an elderly population who may have grossly deficient bone and may struggle to rehabilitate after such injuries.

There is a need for improved devices and methods for treatment of periprosthetic bone fractures. The current invention discloses devices, systems and methods for treating periprosthetic bone fractures while maintaining preexisting implants. The invention is based on an implantable orthopedic device that includes a substantially cylindrical shaft with an opened and expandable proximal portion configured to mate with a distal tip of a preexisting implant in the bone canal.

As used herein the term "distal" refers to the part of the implantable device which, following implantation, is located farthest of the center of the body.

As used herein the term "proximal" refers to the part of the implantable device which, following implantation, is located closest to the center of the body.

As used herein the term "orthopedic implantable device" is interchangeable with the term "subsequent implantable device".

The herein disclosed implantable device is configured to be inserted within the medullary cavity. The herein disclosed implantable device is adjustable and allows an engagement with a preexisting implant or prosthesis in a radial expandable manner. Optionally, the herein disclosed implantable orthopedic device allows a friction match engagement with a preexisting implant or prosthesis. Further optionally, the device of the invention is sized and shaped such that it extends along an entire or along most longitudinal space within the bone canal. The implantable device may be adjustable to comply with various sizes and/or bone canal shapes.

Advantageously, the disclosed implantable device includes an oblique proximal tip allowing readily insertion within the bone canal. This is due to the oblique proximal tip that facilitates paving and/or creating space to the implant within the bone. The oblique proximal tip further advantageously assists in distributing stress concentration at the level of connection of the herein disclosed implantable device with the preexisting implant along the.

The herein disclosed implantable device may be manufactured from various materials, including, but not limited to stainless steel, titanium, cobalt chrome, carbon or any another inert, or biocompatible material. Optionally, the herein disclosed implantable device may be manufactured from a malleable metal.

In one or more embodiments, the shaft has a length of up to about 400 mm. For example, up to about 350 mm, up to about 300 mm, up to about 250 mm, up to about 200 mm, up to about 150 mm, or up to about 100 mm. In one or more embodiments, the shaft has a length within the range of about 50 to about 350 mm.

In one or more embodiments, the implantable device includes at a distal portion thereof cross channels for receiving bone screw(s) allowing fixation of the device to bone without any requirement in auxiliary devices. In one or more embodiments, the implantable device is hollowed and includes engagement means, e.g., a thread, at a distal portion thereof allowing mating with a nail extender to thereby fit various patients. Optionally, the thread at a distal portion of the device can be further facilitated to afford insertion of the device within the bone canal via a dedicated auxiliary device.

The herein disclosed systems and methods can be applicable for the treatment of femur fractures or for the treatment of other long bone fractures having preexisting implants, for example, in the tibia, radius, ulna, humerus, hand or foot.

In an embodiment of the invention, there is provided an orthopedic implantable device which comprises an elongated cylindrical shaft extending between a distal end and a proximal end, the shaft includes a proximal portion, extending from the proximal end, sized and shaped to allow an engagement with a distal tip of a preexisting bone implant, the proximal portion further comprises at least one longitudinal slot extending from the proximal end and allowing the engagement with the preexisting bone implant. The slot extends from the proximal end such that it is open at the proximal end. The slot may present a substantially U-like shape, or V-like shape, or any of the alike shapes.

In one or more embodiments, the slot is longitudinal and parallel to a longitudinal axis of the shaft. Various dimensions (i.e., lengths and widths) of the slot are applicable as long as the proximal portion is maintained relatively flexible and resistant to expansion forces. The slot may present a length of up to about 200 mm. For example, up to about 180 mm, up to about 160 mm, up to about 140 mm, up to about 120 mm, up to about 100 mm, up to about 80 mm, up to about 60 mm or up to about 40 mm. The slot may present a length within the range from about 5 mm to about 170 mm, or within the range from about 5 mm to about 100 mm. The slot may present a maximal width of up to about 20 mm, up to about 10 mm, or up to about 5 mm. For example, the maximal width of the slot is between about 2 mm and about 20 mm.

In one or more embodiments, the proximal portion is expandable due to the existence of the slot, allowing adaptation to various sizes and/or shapes of the distal tip of a preexisting bone implant.

Optionally, the proximal portion has a rounded cross section, or an elliptical cross section. In one or more embodiments, the engagement between the preexisting implant and an orthopedic implantable device of the invention is characterized by a slight radial expansion of the proximal portion of the orthopedic implantable device. In one or more embodiments, the proximal portion may have a conical shape wherein the outer and/or inner diameter(s) decrease(s) from proximal to distal. In one or more embodiments, the proximal end being oblique in a vertical axis of the shaft.

In one or more embodiments, an angle a of less than about 90° extends between a longitudinal axis and a vertical axis of the shaft at the proximal end. In one or more embodiments, the angle a is less than about 85°, or less than about 80°, or less than about 70°, or less than about 60°.

In one or more embodiments, the proximal portion extends from a proximal end toward the distal portion and occupies a length of the shaft of about a third, about a fourth, or about a fifth, or sixth or less, or more, or an intermediate value. In one or more embodiments, the distal portion extends from a distal end towards the proximal portion and occupies a length of the shaft of about a third, about a fourth, or about a fifth, or a sixth, or less, or more, or an intermediate value.

In one or more embodiments, the herein disclosed device can be inserted within a bone canal of a subject utilizing external fixature members/devices/elements known in the art.

The present invention further provides a method for the treatment of periprosthetic bone fracture, the method comprising:

- preparing a bone canal of a fractured bone with a preexisting bone implant, thereby providing space around the preexisting implant;
- inserting an orthopedic implantable device into the bone canal;
- engaging the orthopedic implantable device with the preexisting bone implant; and
- stabilizing a connection between the orthopedic implantable device and the bone.

The step of preparing a bone canal may include enabling a space either around or at the vicinity of a preexisting bone implant to allow the herein disclosed implantable device to engage with the preexisting device. The step of preparing the bone canal may include grinding and/or spitting and/or removing bone tissue. Optionally, preparing a bone canal includes removing tissue material from the bone canal. Optionally, preparing a bone canal includes removing, and/or grinding, and/or spitting a bone cement from the bone canal.

An orthopedic implantable device as herein disclosed can be inserted within the bone using various auxiliary devices, such as, but not limited to an insertion handle. Following insertion of the herein disclosed subsequent implantable device with a preexisting implant, the two implants are coupled until obtaining a stable engagement between the implants. The engagement between the implants may be, but not necessarily, in the form of a friction match between the orthopedic implantable device and the preexisting implant.

Following an engagement between the preexisting device and the herein disclosed subsequent implantable device, the herein disclosed implantable device is stabilized to the bone. Such step of connection to bone/bone fixation may be performed using screws linking the distal portion or distal end of the orthopedic implantable device to the bone.

In an embodiment of the invention, the herein disclosed orthopedic implantable device can be extended to conform to various bone sizes using a nail extender. The nail extender may comprise a longitudinal shaft having a proximal end configured to allow an engagement with the distal end of the orthopedic implantable device. Optionally, the proximal end of the nail extender is having a size and shape being essentially similar to, or slightly smaller than, or slightly larger than the size and shape of the distal end of the orthopedic implantable device. The proximal end of the nail extender is configured to engage with a distal end of the orthopedic implantable device. The nail extender can be stabilized within a bone of a subject via cross screws that can be coupled within dedicated channels allowing connection between the nail extender and the bone of a subject. Optionally, the cross channels configured to receive screws at various angles. For example, an angle of about or up to about 15°, or more, at various directions is applicable. The extender may present various lengths allowing conformity to various bone lengths. Optionally, the nail extender is extendible.

Optionally, one or more adapters can be used to adjust the inner diameter of the proximal end of the implant. Such adaptors may be particularly useful in cases where the preexisting implant has an outermost diameter being less than the inner most diameter of the herein disclosed implantable device, such that the obtained engagement between the implants is spacious. In an embodiment of the invention, the adapter includes a U-like shape. The adapter can present a form of a clip which can catch or hold the wall of the proximal end of the implant. The diameter of the adaptor can be at least about 1 mm. For example, at least about 2 mm, or at least about 3 mm. The adaptor can optionally present a hairpin like structure.

The present invention further provides spatulas sized and shaped to allow insertion thereof within a bone canal (i.e., a medullary cavity). Such spatulas as herein disclosed may optionally include a slight curvature or concavity to conform to bone canals with bows. Thus, the present invention further comprises a spatula for the removal of tissue material from bone cavity, the spatula comprises a handle and a bowl coupled to the handle, the bowl defining a cavity, the spatula sized and shaped to allow insertion thereof within a bone cavity, and the handle comprises a slight curvature to conform to a bow within a bone.

Figures 1, 2:
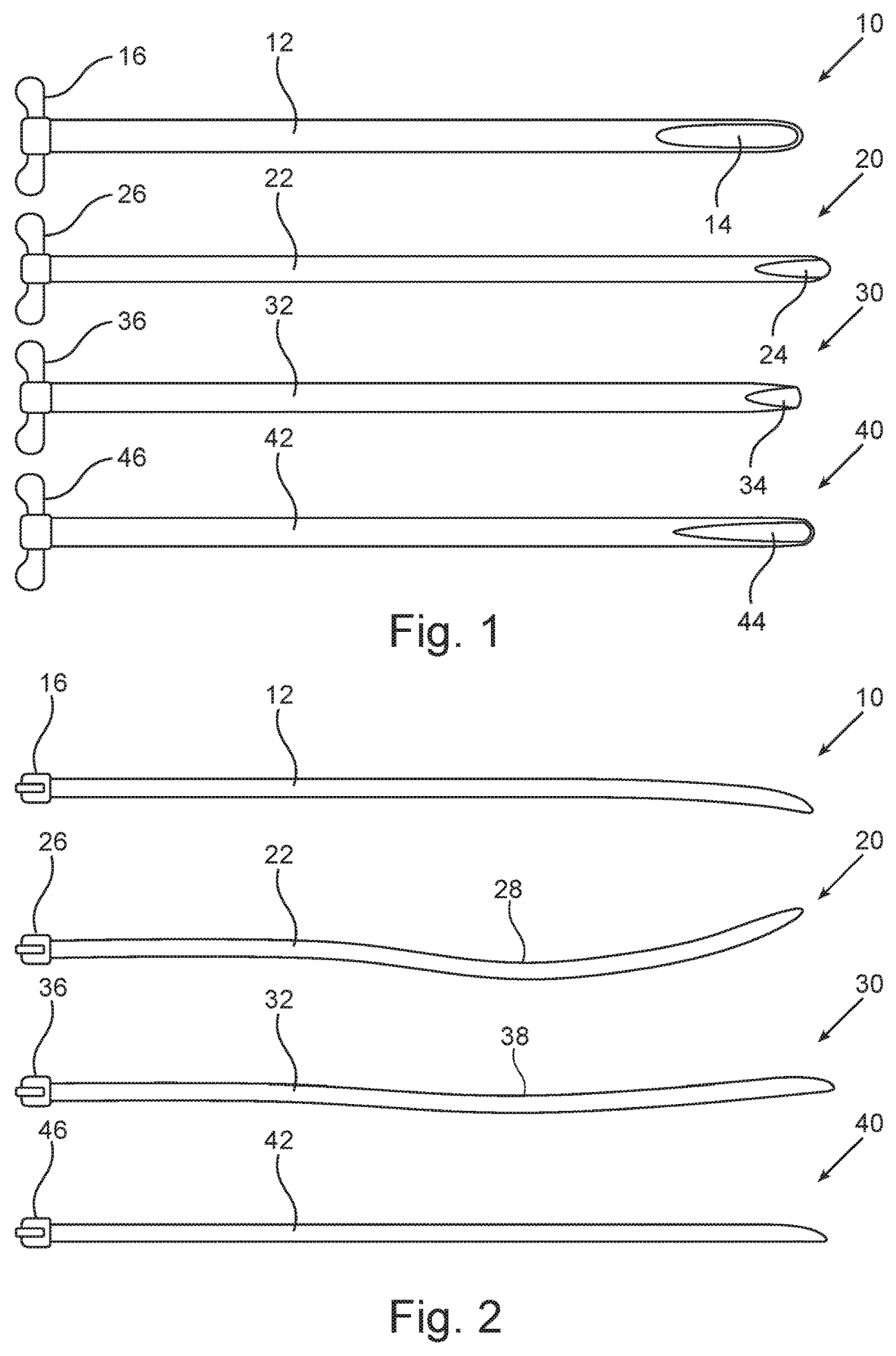

In one or more embodiments, the present invention relates to devices, systems and methods for removing, grinding and/or spitting material from the bone canal. In one or more embodiments, the material is a tissue material, such as bone tissue. In one or more embodiments, the material is a bone cement. As used herein the term "bone cement" refers to a material that fills the free space between a prosthesis and a bone. Bone cement is known to play an important role of an elastic zone. The spatulas shown in FIGS. 1-2 can be used to prepare a bone canal prior to a step of inserting within the bone a prosthesis and/or any other orthopedic device, such as the herein disclosed implantable subsequent device. The preparation of bone, inter alia, includes allowing some space for an implantable device either by removing, grinding and/or spitting the bone.

The herein disclosed spatulas 10, 20, 30, and 40 include handles 12, 22, 32, and 42, and bowls 14, 24, 34, and 44, respectively. Optionally, the handles 22, and 32 include slight curvatures 28 and 38, respectively to conform to a bow within a bone. Optionally, the handles 12, 22, 32, and 42, include a T-like shape, or a T-junction with side wings 16, 26, 36 and 46 which allow convenient grasping and manipulation by a user. The curvature/concavity 28/38 may be a forward curvature (i.e., towards the bow portion). The curvature/concavity may alternatively be a backward curvature (i.e., towards the back side of the spatula). The curvature/concavity 28/38 may have a radius of between about 1 mm and about 100 mm. For example, between about 5 mm and about 80 mm, between about 5 mm and about 60 mm, between about 5 mm and about 40 mm, between about 5 mm and about 20, between about 10 mm and about 100 mm, between about 20 mm and about 100 mm, between about 40 mm and about 100 mm, between about 60 mm and about 100 mm, or between about 80 mm and about 100.

Further advantageously, this invention relates to spatulas which can be readily manipulated to uniformly comply with varying bow curvatures. In an embodiment of the invention, the spatula's bowl and/or handle is manufactured from a resilient material allowing bending thereof during a surgical procedure. Such configuration may be particularly useful for grinding bone canal having various positioning of preexisting bone implants. The spatula could therefore be manufactured from various resilient materials, such as resilient metals, including without limitation titanium.

Bowls 14, 24, 34, and 44 define a cavity. In one or more embodiments, the herein disclosed spatulas are sized and shaped to allow insertion thereof within a bone cavity. In an embodiment of the invention, the herein disclosed spatula is sized and shaped to allow insertion thereof within a long bone cavity. Exemplary long bone cavities include without limitation, cavities within the femur, the tibia, the humerus, the radius and the ulna. In one or more embodiments, the spatulas having a length of at least about 100 mm. In one or more embodiments, the spatulas having a length of up to about 600 mm. In one or more embodiments, the spatulas having a length of between about 100 mm and up to about 500 mm. For example, between about 100 mm and about 400 mm, between about 150 mm and about 500 mm, between about 200 mm and about 300 mm, or between about 400 mm and about 500 mm. In one or more embodiments, the spatula having a width of between about 5 mm and up to about 15 mm. For example, the spatula having a width between about 5 mm and up to about 10 mm. between about 8 mm and about 15 mm.

In one or more embodiments, the length of the bowl portion of the spatula is between about 10 mm and up to about 100 mm. For example, between about 10 mm and about 80 mm, between about 10 mm and 70 mm, between about 10 mm and about 60 mm, between about 10 mm and about 50 mm, between about 20 mm and about 100 mm, between about 30 mm and about 100 mm, between about 40 mm and about 100 mm, or between about 50 mm and about 100 mm.

Reference is now made to FIG. 3 demonstrating an exemplary orthopedic implantable device for the treatment of periprosthetic bone fractures. Device 100 includes an elongated substantially cylindrical shaft 110 extending between a distal end 102 and a proximal end 104. Device 100 is configured to be inserted within the medullary cavity of bones. Shaft 110 may have a length within the range of about 50 to about 350 mm. Optionally, the length of shaft 110 is between about 50 mm to about 300 mm, about 50 mm to about 250 mm, about 50 mm to about 200 mm, about 50 mm to about 150, about 100 mm to about 350 mm, about 150 mm to about 350 mm, about 200 mm to about 350 mm, or about 100 mm to about 300 mm.

Proximal portion 106 extends from proximal end 104 and is sized and shaped to allow an engagement with a distal tip of a preexisting bone implant. Proximal portion 106 extends along about half, third, quarter, fifth, or less, or more the length of shaft 110. Proximal portion 106 includes at least one longitudinal slot 108 extending from and opened at proximal end 104. Slot 108 allows a certain degree of flexibility for the proximal portion 106 affording an engagement with various sizes and/or shapes of bone implants already present within the bone. The slot 108 allows adaptation of the device 100 in a radial expandable manner to various bone implants. In one or more embodiments, the engagement between the preexisting bone implant and device 100 is associated with a friction formed between device 100 and preexisting implant. Slot 108 may present a substantially U-like shape, or a substantially V-like shape. In one or more embodiments, the slot 108 has a length within the range of about 30 mm to about 200 mm. For example, about 30 mm and about 180 mm, about 30 mm and about 160 mm, about 30 mm and about 140 mm, about 30 mm and about 120 mm, about 30 mm and about 100 mm, about 30 mm and about 80 mm, about 30 mm and about 60 mm, about 50 mm and about 200 mm, about 70 mm and about 200 mm, about 90 mm and about 200 mm, about 110 mm and about 200 mm, about 130 mm and about 200 mm, or about 30 mm and about 170 mm. Slot 108 has a maximal width within the range of about 5 mm to about 20 mm. For example, about 5mm and about 15 mm, about 5 mm and about 10 mm, about 10 mm and about 20 mm, or about 15 mm and about 20 mm.

In one or more embodiments, the proximal portion 106 has a rounded cross section (shown for example at FIG. 4B), or an elliptical cross section (shown for example at FIG. 4A). Proximal portion 106 optionally, includes a conical shape wherein the outer and/or inner diameter gradually decreases from proximal end 104. In or more embodiments, shaft 110 is being entirely hollowed, from proximal end 104 to distal end 102. Optionally, at least proximal portion 106 being hollowed. Optionally, at least a portion extending from distal end 102 being hollowed. Further optionally, at least proximal portion and distal portion being hollowed. In one or more embodiments, proximal end 104 is being oblique in a vertical axis of shaft 110 such to form an oblique tip wherein the cross-sectional profile of the tip tapers down from the proximal end towards the distal portion. Advantageously, the oblique tip creating a trowel/scoop-like configuration facilitates easier insertion of the implant within the bone cavity and assists in paving the way for the implant. The oblique tip is essential for creating a space for the implant itself upon insertion thereof within the bone. Further advantageously, the oblique tip assists in distributing stress concentration at the level of connection to a longer part of the implant and allows for an additional medial support. In one or more embodiments, the longest end of the oblique tip is advantageously disposed at the medial side of the bone.

Figure 4B:
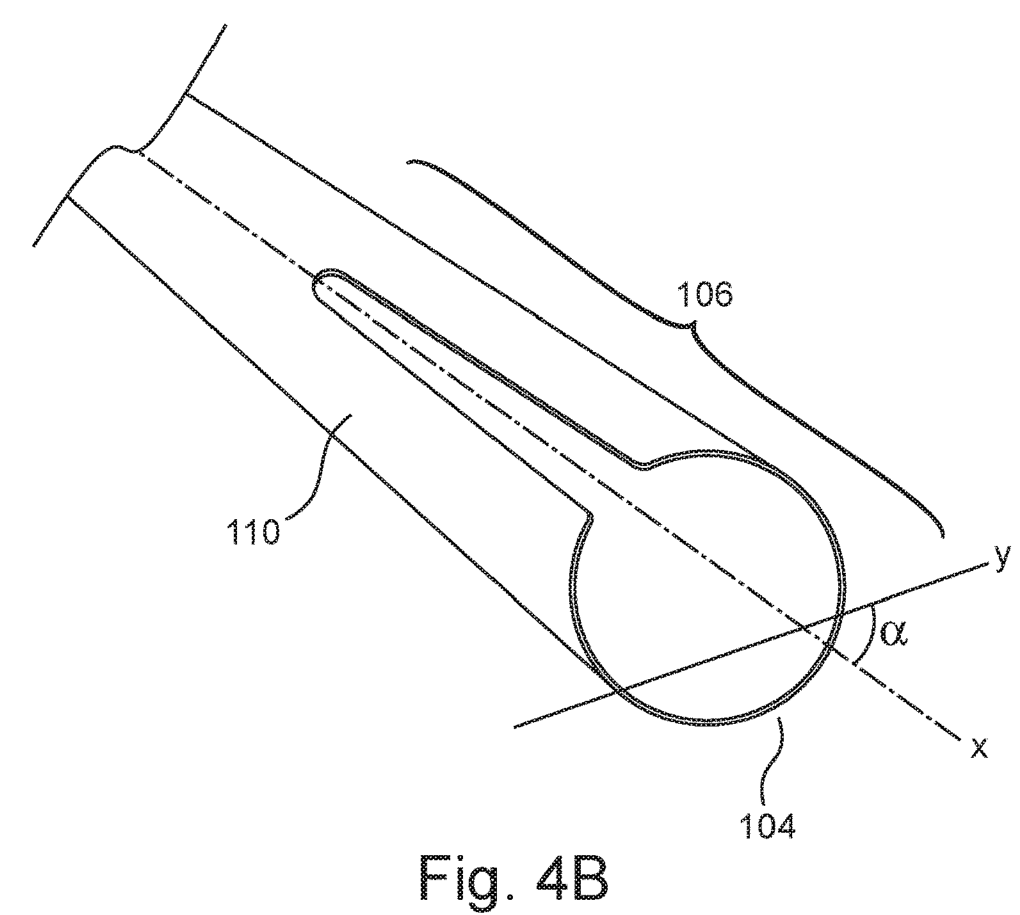

Reference is made to FIGS. 4A-4B, proximal portion of device 100 is shown. An angle a of about, or less than about 90° extends between a longitudinal axis X and a vertical axis Y of the shaft 110 at the proximal end 104. In one or more embodiments, angle a is about or less than about 80°, about or less than about 70°, or about or less than about 60°. To allow engagement with various configurations, and shapes of preexisting bone implants, various shapes of the proximal portion 106 may be provided. For example, the proximal portion 106 may have a rounded cross section (shown for example at FIG. 4B). Alternatively, proximal portion 106 may have an elliptical cross section (shown for example at FIG. 4A).

Figure 5A:
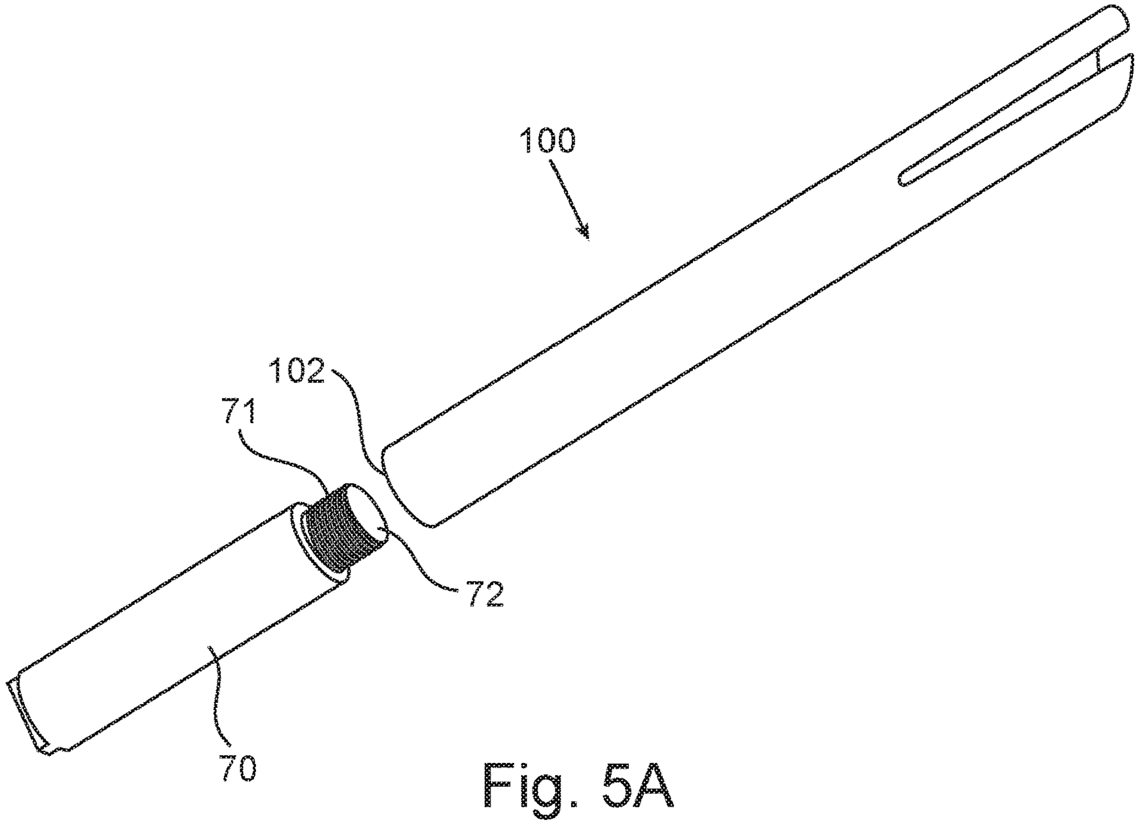
FIGS. 5A-5B are isometric side views illustrating the herein disclosed orthopedic implantable device coupled to a nail extender, according to some embodiments of the invention.
Figure 5B:
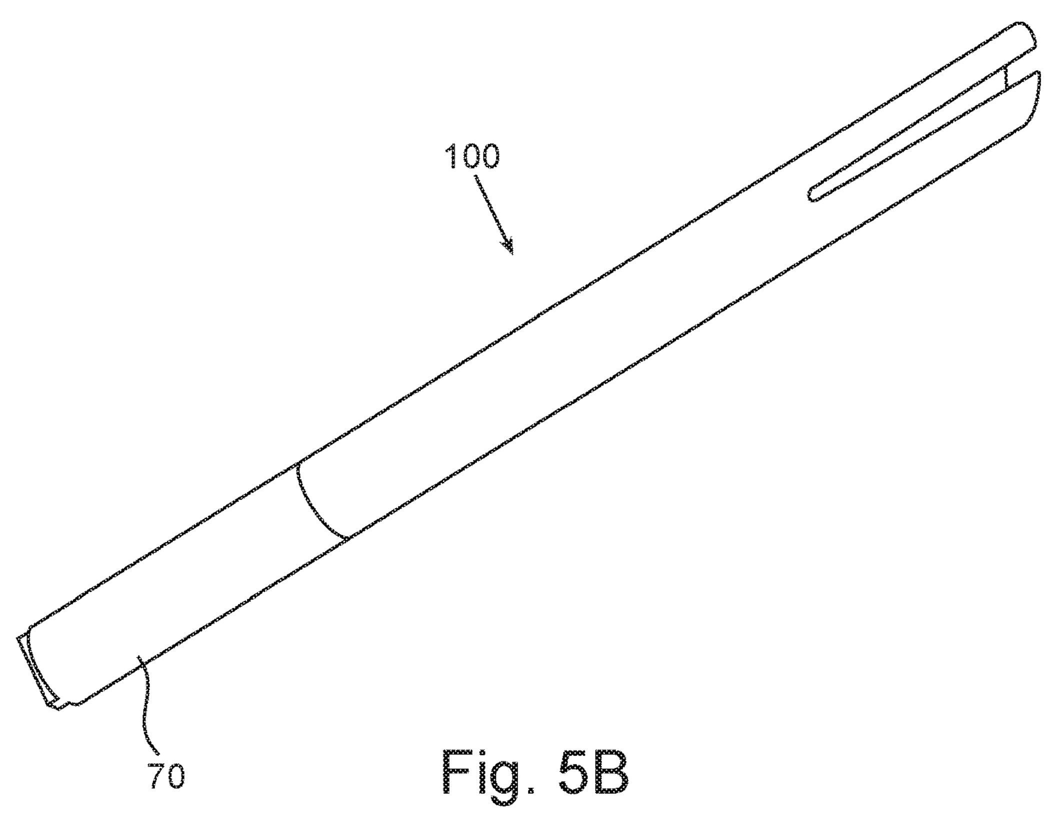

FIGS. 5A-5B demonstrate device 100 which can be extended to adapt various lengths using nail extender 70. Various engagement mechanisms between device 100 and nail extender 70 are contemplated. For example, as shown in FIGS. 5A-5B, device 100 may be engaged with nail extender 70 via a thread 71 present at the proximal end 72 of nail extender 70 and a complementary thread (not shown) within an interior surface of distal end 102 of device 100. At FIG. 5A the nail extender 70 and device 100 are shown when spaced apart. At FIG. 5B the nail extender 70 and device 100 are shown when engaged with each other.

Figure 6:
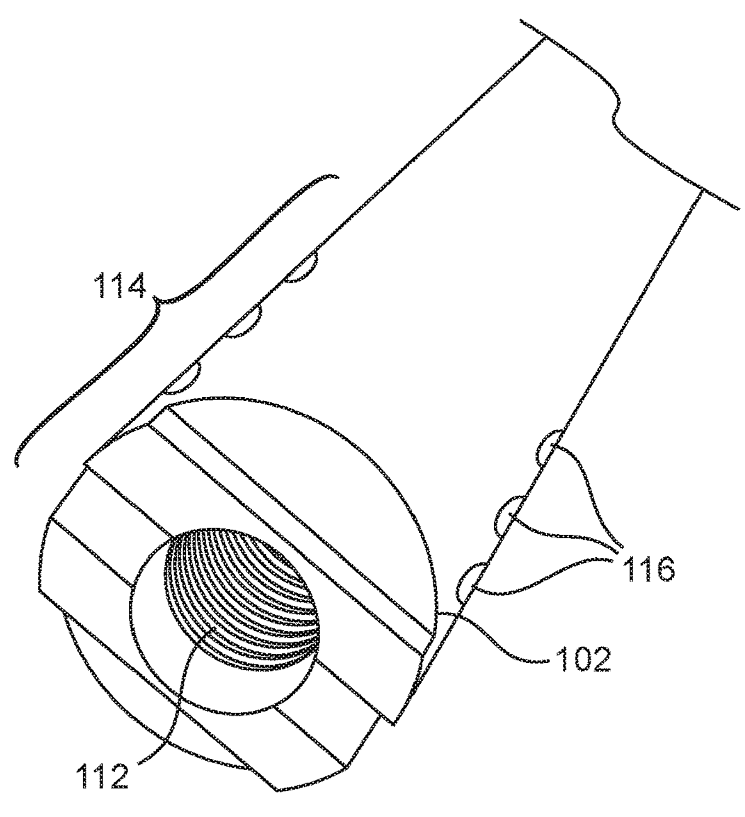
FIG. 6 is an isometric view illustrating a distal portion of the herein disclosed orthopedic implantable device, according to some embodiments of the invention.

FIG. 6 demonstrates distal end 102 of device 100 that is internally threaded including a thread 112 allowing manipulation of the shaft 110 within a bone by a tool comprising a body with complementary external threaded proximal end that can engage with the thread 112. Distal portion 114 further comprising one or more cross channels 116 for receiving bone screw(s), thereby stabilizing shaft 110 within a bone. Various bone screw(s) are applicable. For example, distal portion 114 may include three cross channels 116 for receiving bone screw(s), but a greater number of cross channels 116 for receiving bone screw(s) are applicable. In an exemplary embodiment, distal portion 114 may include four cross channels 116 or a higher number for receiving bone screw(s). For example, the bone screw(s), can be uniplanar or multiplanar.

Figures 7, 8:
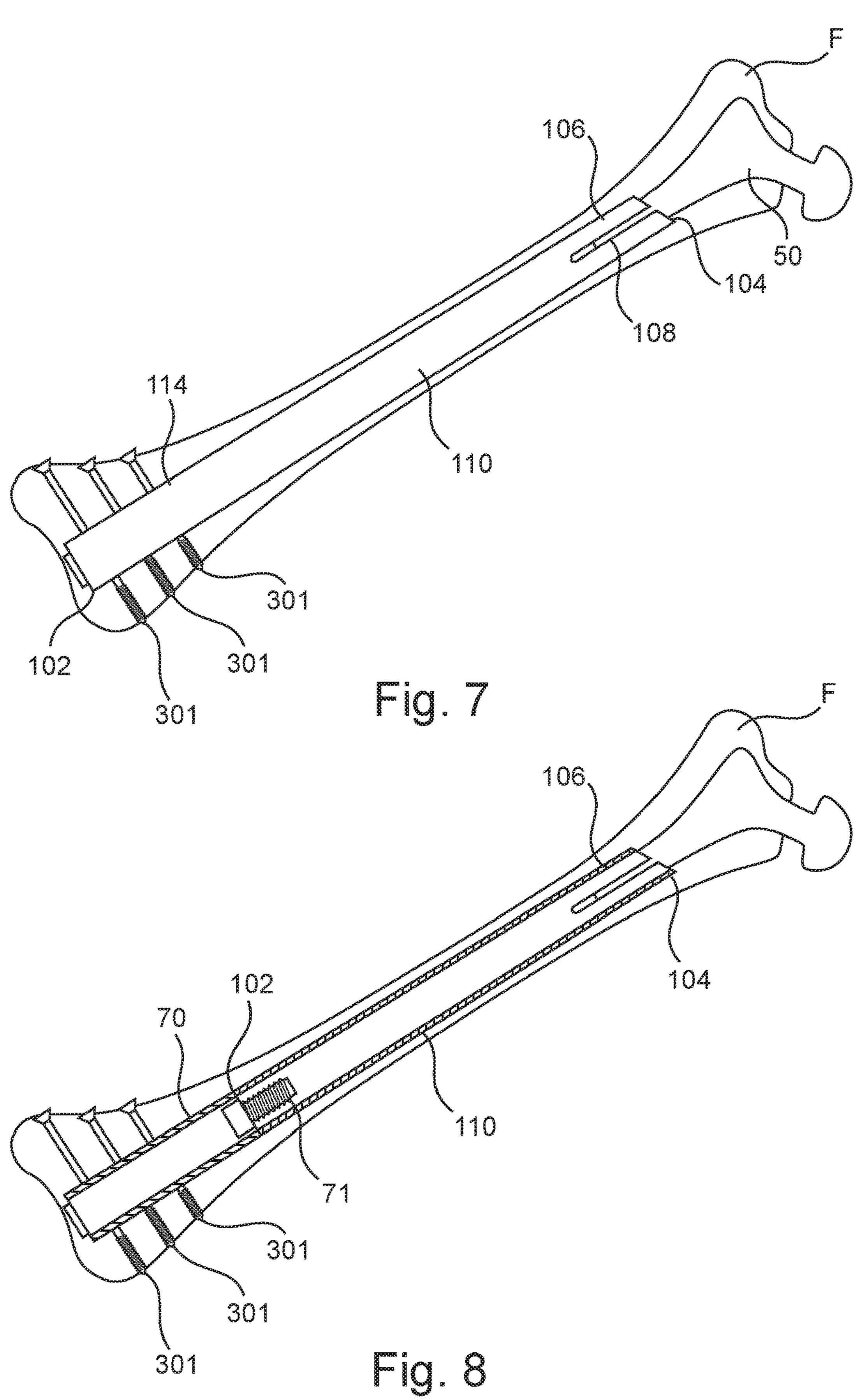
FIG. 7 is a side view of a femur with a preexisting hip prosthesis engaged with the herein disclosed orthopedic implantable device, according to some embodiments of the invention.
FIG. 8 is a cross section view of a femur with a preexisting hip prosthesis engaged with the herein disclosed orthopedic implantable device, which is coupled to a nail extender, according to some embodiments of the invention.

FIG. 7 demonstrates device 100 following implantation thereof within a femoral bone F. Proximal portion 106 is adaptable to various sizes and shapes of bone implants due to the slot 108 which allows a certain flexibility, when engaged with a distal tip or a preexisting bone implant 50. The engagement may allow a friction match connection. Screws 301 may allow stability and fixation of device 100 to the bone.

Figure 9:
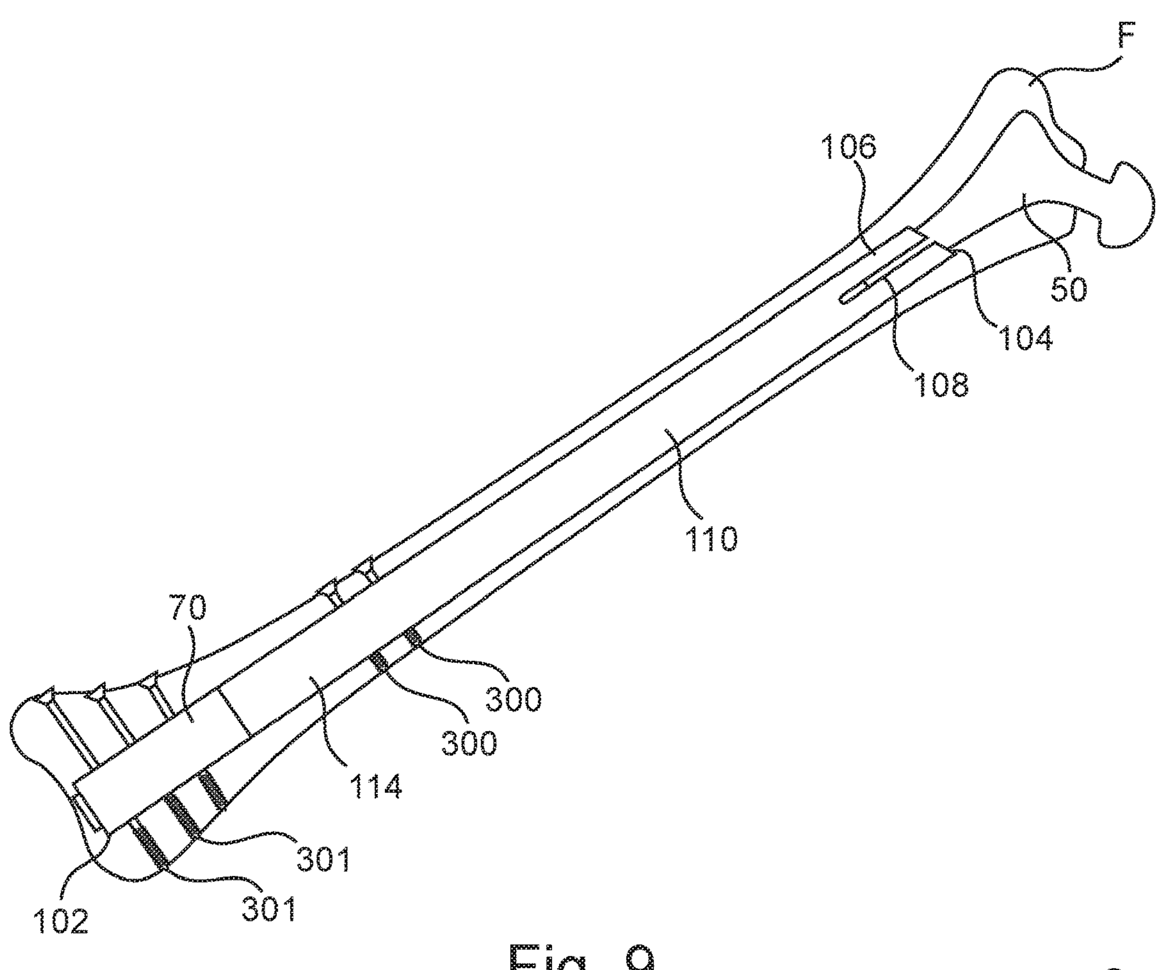
FIG. 9 is a side view of a femur with a preexisting hip prosthesis engaged with the herein disclosed orthopedic implantable device, which is coupled to a nail extender, according to some embodiments of the invention.

Referring now to FIGS. 8-9, device 100 is shown following implantation thereof within a femoral bone F. In this case, femoral bone F is longer and the device 100 is expanded using a nail extender 70 which can be coupled to distal end 102 of device 100. Nail extender 70 includes cross channels 116 configured to receive screws 301, allowing fixation of the extender 70 to bone F. Optionally, or additionally, device 100 includes cross channels 116 for accommodating screws 300, thereby fixating device 100 to bone F.

Figure 10:
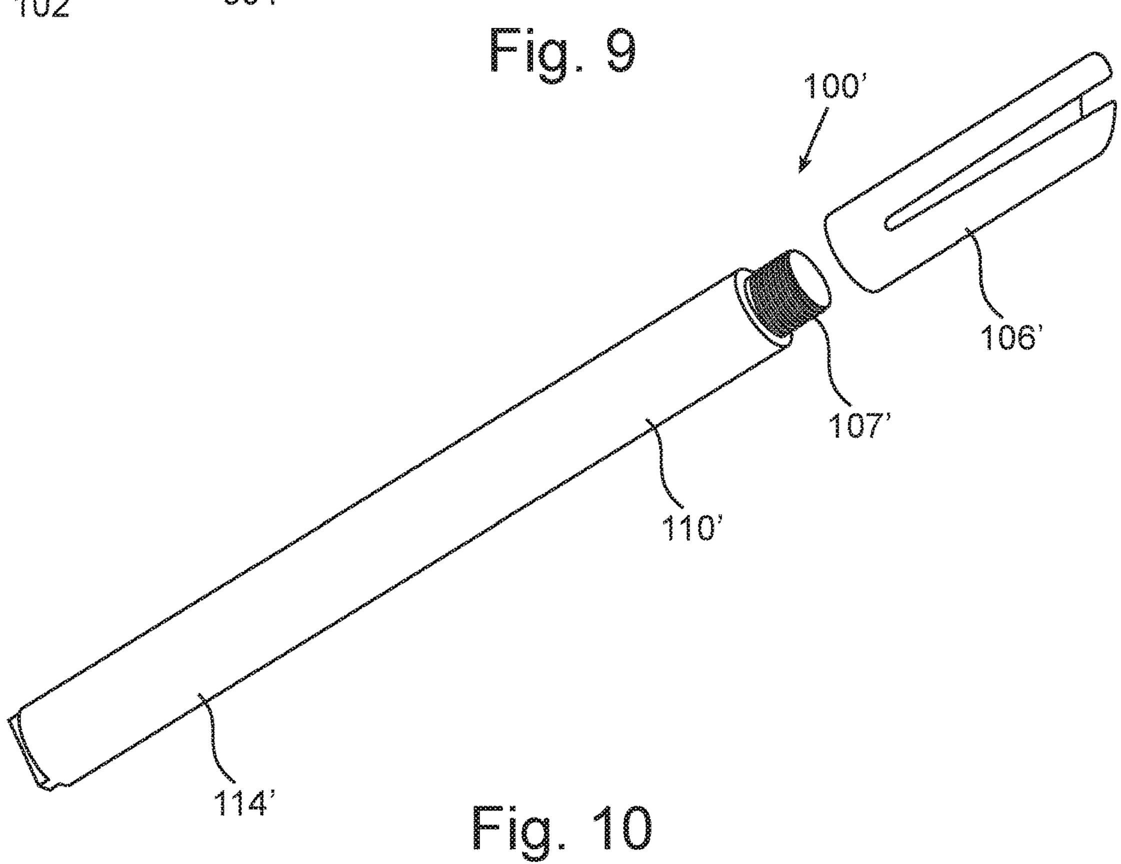
FIG. 10 is a side view illustrating an exchangeable proximal portion of the herein disclosed orthopedic implantable device, according to some embodiments of the invention.

FIG. 10 demonstrates another exemplary device 100' which includes an exchangeable proximal portion 106'. In this case, the proximal portion can be replaced with other types/sizes/shapes of proximal portions, having for example, a rounded or an elliptic cross section (see FIGS. 4A-4B), allowing an engagement with various sizes and shapes of preexisting bone implants. Exchangeable proximal portion 106' may be engaged with shaft 110' via thread 107' disposed at a proximal end of shaft 110' and complementary thread present at distal end of portion 106' (not shown). Although a thread type engagement is herein shown to connect exchangeable proximal portion 106' to shaft 110', but other types of engagement mechanisms are further contemplated.

Each of the following terms: 'includes', 'including', 'has', 'having', 'comprises', and 'comprising', and, their linguistic, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

Each of the phrases 'consisting of' and 'consists of', as used herein, means 'including and limited to'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', is some embodiments, refers to ±30% of the stated numerical value. In further embodiments, the term refers to ±20% of the stated numerical value. In yet further embodiments, the term refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for the treatment of a periprosthetic bone fracture, the method comprising:

preparing a medullary cavity of a fractured femur with a preexisting hip prosthesis;

providing an orthopedic implantable device comprising an elongated cylindrical shaft extending between a distal end and a proximal end and having a longitudinal axis, wherein the device is configured to be inserted within the medullary cavity of the femur, wherein a proximal portion of the device extends from the proximal end, the proximal portion being sized and shaped to allow radial engagement with a distal tip of the preexisting hip prosthesis through a friction fit, wherein said elongated cylindrical shaft is oblique relative to a vertical axis of said proximal end, thereby forming an oblique tip, and wherein said device is configured for positioning such that a long end of said longitudinal axis of the oblique tip is disposed at a medial side of the femur;

inserting said orthopedic implantable device into said medullary cavity such that the long end of said oblique tip is disposed at said medial side of said femur;

radially engaging said orthopedic implantable device with said distal tip of said preexisting hip prosthesis, through a friction fit; and stabilizing connection of said orthopedic implantable device to the bone.

2. The method according to claim 1, wherein the step of preparing a medullary cavity comprises removing a tissue material from the medullary cavity, to thereby allow space around the preexisting hip prosthesis.

3. The method according to claim 1, further comprising expanding the orthopedic implantable device using a nail extender, the nail extender comprises a longitudinal shaft having a proximal end configured to engage with a distal end of the orthopedic implantable device.

4. The method according to claim 3, wherein the nail extender includes a connection bolt allowing to secure the connection between the distal end of the orthopedic implantable device and the proximal end of the nail extender.

* * * * *